United States Patent [19]

Beck et al.

[11] Patent Number: 5,684,185
[45] Date of Patent: Nov. 4, 1997

[54] PROCESS FOR THE STEREOSELECTIVE SYNTHESIS OF 3-SUBSTITUTED 2-SULFONYLMETHYLPROPIONIC ACIDS, AND INTERMEDIATE PRODUCTS

[75] Inventors: Gerhard Beck; Joachim-Heiner Jendralla; Bernhard Kammermeier, all of Frankfurt am Main, Germany

[73] Assignee: Hoechst Aktiengesellschaft, Frankfurt am Main, Germany

[21] Appl. No.: 411,832

[22] PCT Filed: Sep. 30, 1993

[86] PCT No.: PCT/EP93/02674

§ 371 Date: Mar. 30, 1995

§ 102(e) Date: Mar. 30, 1995

[87] PCT Pub. No.: WO94/07850

PCT Pub. Date: Apr. 14, 1994

[30] Foreign Application Priority Data

Oct. 1, 1992 [DE] Germany .................. 42 33 100.5

[51] Int. Cl.$^6$ ................... C07C 315/00
[52] U.S. Cl. ............. 562/427; 562/401; 562/429
[58] Field of Search ............... 562/401, 427, 562/429

[56] References Cited

U.S. PATENT DOCUMENTS 4,758,584  7/1988  Bühlmayer et al. .
5,554,788  9/1996  Holla et al. ............... 562/429

FOREIGN PATENT DOCUMENTS 0 309 766 A3  4/1989  European Pat. Off. .
WO 92/03132  3/1992  WIPO .

OTHER PUBLICATIONS

"Synthesis and Biological Activity of Some Transition–State Inhibitors of Human Renin", Peter Bühlmayer et al., Journal of Medicinal Chemistry, 31 (9):1839–1846 (1988).

"Preparation of 2-(Alkylthiomethyl)acrylates", M.F. Semmelhack et al., Journal Of Organic Chemistry, 43 (6):1259–1262 (1978).

"Synthesis of (3–Ethoxycarbonyl but–3–en–2–yl)Phenyl Sulfone and (2–Ethoxycarbonyl but–2–en–1–yl) Phenyl Sulfone From Ethyl 2–Bromomethyl but–2–enoate", D. Colombani et al., Synthetic Communications, 21 (14):1481–1487 (1991).

"Necic Acid Synthons. Part7.$^1$2–Substituted Acrylate Systems. Useful Extensions to the 1,4–diazabicyclo[2.2.2]octane–derived Cascade", Farouk Ameer et al., South African Journal of Chemistry, 40(1):35–38 (1987).

"Formation Of A Novel Thiopyranoindole Ring System", J. Hutchinson et al., Tetrahedron Letters, 33(33):4713–4716 (1992).

Primary Examiner—Samuel Barts
Attorney, Agent, or Firm—Finnegan, Henderson, Farabow, Garrett & Dunner, L.L.P.

[57] ABSTRACT

Compounds of the formula I

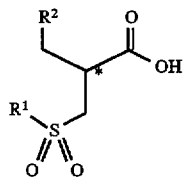

can be prepared in a multi-day process starting from the compounds of the formulae II and III

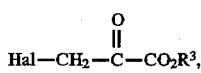

where the substituents $R^1$, $R^2$ and $R^3$ have the meanings given.

3 Claims, No Drawings

PROCESS FOR THE STEREOSELECTIVE SYNTHESIS OF 3-SUBSTITUTED 2-SULFONYLMETHYLPROPIONIC ACIDS, AND INTERMEDIATE PRODUCTS

This application is a 371 of PCT/EP93/02674 filed Sep. 30, 1993.

3-Substituted 2-sulfonylmethylpropionic acids and derivatives thereof, for example esters, are gaining interest as building blocks and as precursors for aspartyl protease inhibitors [P. Bühlmeyer et al., J. Med. Chem. 31 (1988), 1839; R. Henning, Nachr. Chem. Techn. Lab. 38 (1990), 460; J. R. Huff, J. Med. Chem. 34 (1991), 2305].

The compounds mentioned are already known, moreover, a series of syntheses or processes for the preparation of these compounds has been described.

In this context, examples of some recent works include:

P. Bühlmeyer et al., J. Med. Chem. 31 (1988), 1839;
K. Tsuji et al., Tetrahedron Lett. 30 (1989), 6189;
M. Nakano et al., Tetrahedron Lett. 31 (1990), 1569;
M. Nakano et al., Chem. Lett. (1990), 505; cf. also
D. A. Evans et al., J. Org. Chem. 50 (1985), 1830.

The first-mentioned synthesis requires, inter alia, the use of formaldehyde and/or formaldehyde derivatives, which, like the by-products formed in this case, are regarded as being highly objectionable in terms of health because of their alkylating properties and necessitate specific safety measures which include the area of workplace health and safety [Merck Index 11, 4150].

Moreover, the preparation of optically pure compounds requires the splitting of a racemate. For this purpose the racemic acid is converted into the diastereomeric amides using L-phenylalaninol, these amides are separated by chromatography, and the desired isomer is obtained by hydrolysis of the corresponding amide. The large number of steps, fundamental disadvantages of splitting a racemate and the scale-up problems involved in a chromatographic purification mean that this route appears unattractive for the preparation of relatively large quantities.

The synthesis according to Tsuyi et al. leads to optically pure material with a similar number of steps but without splitting a racemate. This synthesis comprises a number of steps for the introduction and elimination of protecting groups; some of the reagents employed are expensive, and in some cases carcinogenic formaldehyde derivatives are used or produced in the course of the syntheses [H. G. Neumann in "Allgemeine und spezielle Pharmakologie und Toxikologie" [General and specific pharmacology and toxicology], 4th edition, W. Forth, Ed., B. I. Wissenschaftsverlag, Mannheim-Vienna-Zurich, p. 621 ff (1983); Arch. Environ. Health 30 (2), 61].

Therefore, this synthesis route does not constitute an economically and ecologically justifiable alternative for the preparation of large quantities.

The preparation of 2-mercaptomethyldihydrocinnamic acid, which is shown in the context of the synthesis of thiorphan described by Evans and Mathre, is short in comparison with the two syntheses which have already been discussed and proceeds with a good overall yield, and enables the specific preparation of both enantiomers in high optical purity. The weak point in the synthesis is the complex introduction of the mercaptan grouping and the consequent necessity to use benzylthiomethyl bromide, which is objectional in terms of health and is prepared from trioxane (as formaldehyde source), benzyl mercaptan (or benzylthiomethyl chloride) and HBr [H. G. Neumann in "Allgemeine und spezielle Pharmakologie und Toxikologie" [General and specific pharmacology and toxicology], 4th edition, W. Forth, Ed., B. I. Wissenschaftsverlag, Mannheim-Vienna-Zurich, p- 621 ff (1983); Arch. Environ. Health 30 (2), 61].

Nakano et al. describe two routes for the synthesis of the carbon framework of the compounds I. The first synthesis starts from diethyl malonate, and requires six steps and, in addition, chromatographic resolution of the diastereomers.

The second route proceeds via a chiral, non-racemic arylpropionyloxazolidinone and its stereoselective alkylation using benzyl bromomethyl ether [M. W. Holladay et al., J. Med. Chem. 30 (1987), 374] followed by chromatography. After removal of the benzyl group by hydrogenation, as in the case of the first route, the sulfur substituent is introduced by tosylation of the free hydroxyl group followed by substitution with $NaSCH_2CH_3$ in DMF.

These two synthesis routes are also characterized by: a high number of steps, carcinogenic and toxic formaldehyde derivatives as precursors or reagents, the complex introduction of the sulfur substituent, which is a procedure which is not entirely free from racemization, and, last but not least, the chromatographic separation of impurities and resolution of diastereomeric compounds.

The object on which the present invention is based is to develop a process for the synthesis of compounds of the formula I which has a low number of steps,
does not require protecting-group chemistry,
does not require column chromatography steps,
is stereoselective and leads selectively to the enantiomeric compounds of the formula I,
does not require splitting of racemates or resolution of diastereomers, and
represents an improvement, or is unobjectional, from the points of view of health, ecology and safety.

This object is achieved by the process according to the invention. The subject of the invention is consequently a process for the stereoselective preparation of a compound of the formula I

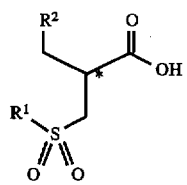

in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which may be substituted by 1, 2 or 3 identical or different hydroxyl, methoxy or trialkylsilyloxy groups; and $R^2$ is $C_6$–$C_{12}$-aryl which may be substituted by 1, 2 or 3 identical or different methoxy, halogen, cyano, methyl, trifluoromethyl, isopropyl or nitro groups; is $C_3$–$C_9$-heteroaryl which may be substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which may be substituted by 1, 2 or 3 identical or different methoxy, halogen, cyano, methyl, trifluoromethyl, isopropyl or nitro groups and the compounds of the formula I may be present in the R or S form, which comprises I) reacting mercaptans of the formula II $R^1$—SH            II in which $R^1$ is as defined for the formula I in the presence of a base with a compound of the formula III

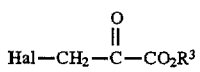
III in which Hal may be iodine, bromine or chlorine and $R^3$ may be a straight-chain or branched alkyl radical having 1 to 6 carbon atoms, to give a compound of the formula IV

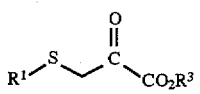
IV in which $R^1$ is as defined for formula I and $R^3$ is as defined for formula III, and II) reacting the compounds of the formula IV with ylides of the formula V $$R^2-CH=P\,(C_6H_5)_3 \quad V$$

in which $R^2$ is as defined for the formula I, to give the unsaturated compounds of the formula VI

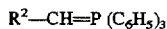
VI in which $R^1$ and $R^2$ are as defined for formula I and $R^3$ is as defined for formula III, and III) converting the compounds of the formula VI into compounds of the formula I, by A) subjecting the compounds of the formula VI to alkaline hydrolysis to give compounds of the formula VII

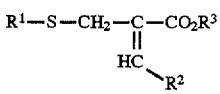
VII in which $R^1$ and $R^2$ are as defined for the formula I, and a) by enantioselective hydrogenation, converting compounds of the formula VII into compounds of the formula X

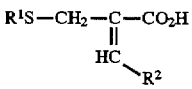
X in which $R^1$ and $R^2$ are as defined for the formula I, and, by subsequent oxidation, converting compounds of the formula X into compounds of the formula I, or b) by oxidation, reacting compounds of the formula VII to give compounds of the formula XI

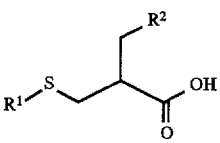
XI in which $R^1$ and $R^2$ are as defined for the formula I, and, by subsequent enantioselective hydrogenation of the compounds of the formula XI, obtaining compounds of the formula I, or B) subjecting the compounds of the formula VI to enantioselective hydrogenation with chiral catalysts to give the compounds of the formula VIII

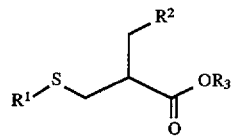
VIII in which $R^1$ and $R^2$ are as defined for the formula I and $R^3$ is as defined for the formula III, and a) by alkaline hydrolysis, converting compounds of the formula VIII into compounds of the formula X

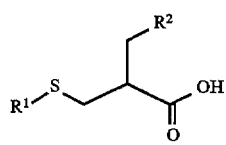
X in which $R^1$ and $R^2$ are as defined for the formula I and, by subsequent oxidation of the compounds of the formula X, obtaining compounds of the formula I, or b) by oxidation of the compounds of the formula VIII, obtaining compounds of the formula XII

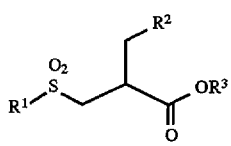
XII in which $R^1$ and $R^2$ are as defined for the formula I and $R^3$ is as defined for the formula III, and subsequently, by alkaline hydrolysis, converting compounds of the formula XII into compounds of the formula I, or c) oxidizing the compounds of the formula VI to give the compounds of the formula IX

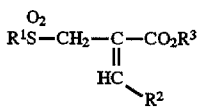
IX in which $R^1$ and $R^2$ are as defined for the formula I and $R^3$ is as defined for the formula III, and converting the compounds of the formula IX into compounds of the formula I by a) alkaline hydrolysis of the compounds of the formula IX to give compounds of the formula XI,

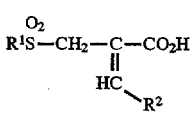
XI in which $R^1$ and $R^2$ are as defined for the formula I, and subsequent enantioselective hydrogenation of the compounds of the formula XI to give compounds of the formula I, or b) enantioselective hydrogenation of the compounds of the formula IX to give compounds of the formula XII

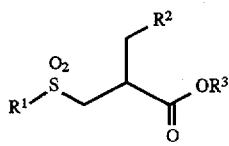

in which $R^1$ and $R^2$ are as defined for the formula I and $R^3$ is as defined for the formula III, and subsequent alkaline hydrolysis of the compounds of the formula XII to give compounds of the formula I.

The process according to the invention is particularly suitable for the preparation of compounds of the formula I in which $R^1$ is $C_1$–$C_4$-alkyl, $C_5$–$C_6$-cycloalkyl, $(C_6$–$C_{12})$-aryl-$(C_1$–$C_3)$-alkyl or $C_6$–$C_{12}$-aryl or heteroaryl, which may be substituted by a hydroxyl, methoxy or trialkylsilyloxy group; and $R^2$ is $C_6$–$C_{12}$-aryl which may be substituted by a methoxy, halogen, methyl, trifluoromethyl or isopropyl group;

is $C_3$–$C_6$-heteroaryl which may be substituted by a methoxy, halogen, methyl, trifluoromethyl, or isopropyl group, or is $C_1$–$C_4$-alkyl, -alkenyl or -alkynyl.

The process according to the invention is very particularly suitable for the preparation of compounds of the formula I in which $R^1$ is $C_1$–$C_4$-alkyl, $(C_6$–$C_{12})$-aryl-$(C_1$–$C_3)$-alkyl or $C_6$–$C_{12}$-aryl, and $R^2$ is $C_6$–$C_{12}$-aryl, $C_3$–$C_6$-heteroaryl or $C_1$–$C_4$-alkyl, -alkenyl or -alkynyl.

Further subjects of the present invention are compounds of the formula IV

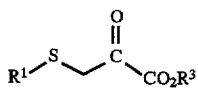

in which $R^1$ and $R^3$ are as defined in claim 1, compounds of the formula VI

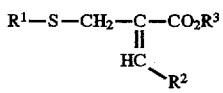

in which $R^1$, $R^2$ and $R^3$ are as defined in claim 1, compounds of the formula VII

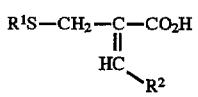

in which $R^1$ and $R^2$ are as defined in claim 1, compounds of the formula VIII

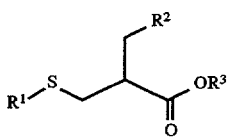

in which $R^1$, $R^2$ and $R^3$ are as defined in claim 1, compounds of the formula IX

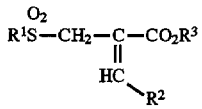

in which $R^1$, $R^2$ and $R^3$ are as defined in claim 1, compounds of the formula X

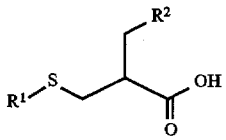

in which $R^1$ and $R^2$ are as defined in claim 1, compounds of the formula XI

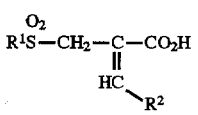

in which $R^1$ and $R^2$ are as defined in claim 1, and compounds of the formula XII

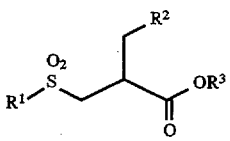

in which $R^1$, $R^2$ and $R^3$ are as defined in claim 1.

A further subject of the present invention are the processes for the preparation of the compounds of the formulae IV, VI, VII, VIII, IX, X, XI and XII, in which the substituents are as defined in claim 1, in accordance with the process steps described above.

The compounds of the formulae I, VIII, X and XII may be present in R or S form.

The compounds of the formulae VI, VII, IX and XI may be present as E (trans) or Z (cis) isomers.

The mercaptans of the formula II which are employed as starting materials in the process according to the invention are commercially available (e.g. Fluka, Aldrich) or can be prepared by methods known from the literature (e.g. Organikum, Verlag VEB Berlin 1964, p. 176 and B. O. Isler et al. Helv. Chim. Acta 108, 903 (1956) or according to R. P. Valante, Tetrahedron Lett. 22, 3119 (1981). The corresponding pyruvic acid derivatives of the formula III can be prepared by analogy with the method of E. Cadis et al., CA 193 (21): 190763 g or according to N. F. Blau, I. Org. Chem. 22, 83 (1957), but are also commercially available (e.g. Fluka).

The subsequent S-alkylation of the mercaptans II with the compounds of the formula III to give the compounds of the formula IV is carried out in the presence of bases such as, for example, NaOH, KOH, $NEt_3$, NaH and sodium ethylate, preferably in an organic solvent such as tetrahydrofuran, acetone or DME at temperatures of between 0° C. and +70° C. over 1 to 6 hours. A preferred embodiment comprises employing a two-phase catalysis in water/methylene chloride in the presence of $NaHCO_3$ as base and a phase-transfer catalyst.

The phosphorus ylides of the formula V are, for example, prepared in situ from the corresponding phosphonium salts in the presence of bases such as NaH, K tert-butylate, Na ethylate or NaOH, for example, in a solvent such as, for example tetrahydrofuran, DME or DMSO at temperatures of from −10° C. to +60° C.

The reaction of the ylides V with the keto compounds of the formula IV is carried out by a Wittig reaction (overview: B. E. Maryanoff, A. B. Reitz Phosphorus and Sulfur 27, 167 (1986) and Chem. Rev. 89, 863 (1989)) for example in solvents such as DMSO, tetrahydrofuran, DME or the like at temperatures of from −10° C. to +80° C.

In order to prepare the compounds of the formula VII according to the invention, the compounds of the formula VI are preferably dissolved in solvents such as, for example, alcohols, DME/$H_2O$ or dipolar aprotic solvents such as DMF, acetonitrile and DMSO, two or more equivalents of $K_2CO_3$ or NaOH are added, and the mixture is subjected to hydrolysis at temperatures of from 0° C. to +40° C. for from 1 to 2 hours. A preferred embodiment comprises dissolving the starting compounds in methanol or ethanol and carrying out treatment with from 2 to 4 equivalents of potassium carbonate at room temperature over 2 hours.

The conversion of compounds of the formula VI into compounds of the formula VIII is carried out by means of enantioselective hydrogenation.

It is known that, in principle, heterogeneous enantioselective hydrogenations can be achieved with an enantiomeric excess of >90% ee over Raney nickel catalysts which have been modified with tartaric acid and sodium bromide (T. Harada et al., Chem. Lett. 1195 (1978); A. Tai et al., Chem. Lett. 2083 (1984)). However, because of the known allergenic potential of nickel and the poor reproducibility of the method, such heterogeneous catalysts are unsuitable, for example, for the synthesis of pharmaceuticals.

In accordance with the present invention, therefore, the optical induction is obtained by the use of a dissolved, optically pure, organometallic complex as hydrogenation catalyst. The catalyst need only be present in the reaction mixture at a low concentration. The molar ratios of converted substrate to catalyst employed are in general, depending on the catalyst and the substrate, between 100 and about 50,000, preferably between 100 and 5000. The upper limit to the substrate/catalyst ratio is determined essentially by the fact that the "active catalyst" which is present under hydrogenating conditions is generally consumed rapidly and irreversibly by oxygen. The quantity of catalyst required therefore depends essentially on the extent to which the reaction solution can be degassed before hydrogenation begins and the extent to which air can be excluded while the hydrogenation is taking place [see e.g. W. Vocke et al., Chem. Techn. 39, 123 (1987)].

From about 0.1 to 0.5 mol % of catalyst are generally sufficient. In the complexes which are preferably employed, the central atom is either a rhodium(I) cation or a ruthenium (II) cation.

Before beginning hydrogenation it is preferred to place a solution of the substrate, of the precatalyst and, if desired, of additives (e.g. of an amine) in a suitable inert solvent or solvent mixture. The degassed solution is then shaken or stirred under from 1 to 500 atm, preferably under from 1 to 150 atm, of hydrogen gas.

Instead of hydrogen gas it is also possible to employ a transfer hydrogenation in the presence of a hydrogen source, for example formic acid/triethylamine or isopropanol.

The principle of the enantioselective transfer hydrogenation of C=C double bonds has been described by H. Brunner et al. [J. Organomet. Chem. 387, 209 (1990), Tetrahedron: Asymmetry 2, 331 (1991)].

Depending on the substrate and catalyst, the hydrogenation can be carried out, for example, within the temperature range from about −40° C. to +200° C. The extent of hydrogenation can be monitored by measuring the consumption of hydrogen or by HPLC analysis. The enantioselectivity of the hydrogenation of a given substrate which can be determined empirically is affected by parameters such as reaction temperature, hydrogen pressure, nature of the solvent, presence of additives, sometimes to a considerable extent. For example, the enantioselectivity of some optically active rhodium(I) diphosphine complexes is markedly reduced if a certain limiting pressure of hydrogen is exceeded (see e.g. H. Takaheshi, K. Achiwa, Chem. Lett., 1921 (1987)), whereas if a different kind of diphosphine is present the enantiomeric excess (ee) of the product either remains unaffected (see e.g. U. Nagel et al., Chem. Ber. 119, 3326 (1986)) or even increases (see e.g. A. Chan, WO 90/15790, Monsanto). Chan demonstrated, in the form of extensive tables, that, in the case of the asymmetric hydrogenation of α-aryl-propionic acids using different ruthenium-BINAP catalysts, the optical purity of the hydrogenation product always increases as the hydrogen pressure rises and the reaction temperature falls. In general, the rate of hydrogenation increases as the hydrogen pressure rises, and less catalyst is required. A temperature increase also generally leads to an acceleration of hydrogenation, but is often associated with a reduction in the enantiomeric excess and a shorter catalyst life. In many cases, however, the optimum result is achieved by increasing the temperature and reducing the hydrogenation time (see e.g. M. Kitamura et al., Tetrahedron Lett. 29, 1555 (1988)). The enantioselectivity of the hydrogenation of a given substrate/catalyst pairing can often be enhanced by cooling at from −20° C. to 0° C., though taking into account a longer period of hydrogenation (e.g. A. Chan, loc. cit.). Difficult to calculate, but in some cases significant, is the effect of an additive such as, for example, triethylamine or optically active 1-phenylethylamine on the enantioselectivity of the asymmetric hydrogenation. Whereas, for example, the hydrogenation of phenylitaconic acids with the rhodium complex of BPPM only leads to benzylsuccinic acids with high enantiomeric excess in the presence of an equivalent of an amine, for some other substrate/catalyst pairings the enantiomeric excess remains unaffected in the presence of triethylamine or even, in a few cases, falls sharply.

Another factor to be determined empirically is the effect of a cationic precatalyst as compared with a neutral precatalyst for a given metal ($Rh^I$ or $Ru^{II}$) and a given optically active diphosphine. In the majority of cases the cationic rhodium(I) complexes have a higher catalytic activity and a greater enantioselectivity than corresponding neutral complexes. In some cases, however, the relationships are reversed.

Suitable solvents for the asymmetric hydrogenation are in principle all liquids which dissolve substrate, catalyst and any additives added and are inert under the reaction conditions. These prerequisites are met, inter alia, by unbranched and branched alcohols. Of these, methanol, ethanol, propanol or isopropanol are preferred because of the ease with which they can be removed in vacuo. Some catalysts, however, exhibit increasing enantioselectivity with falling solvent polarity, and thus give products with a higher enantiomeric excess in isopropanol than in methanol. In such cases it is advantageous to add a nonpolar co-solvent which is miscible with the alcohol or to carry out the hydrogenation directly in a solvent of low polarity.

A review of known chiral diphosphines and the use of their rhodium(I) or ruthenium(II) complexes for the asymmetric hydrogenation of C=C double bonds can be found in:

a) K. E. Koenig in "Asymmetric Synthesis", Vol. 5, Ed. Morrison, J. D. Academic Press, Orlando 1985, page 71, ff b) J. W. ApSimon et al., Tetrahedron 42, 5157 (1986), page 5173 to 5186;

c) H. Brunner, Top. Stereochem. 18, 129 (1988);

d) I. Ojima et al., Tetrahedron 45, 6901 (1989), page 6902 to 6916;

e) R. Noyori, H. Takaya, Acc. Chem. Res. 23, 345 (1990);

f) H. Takaya et al., Pure & Appl. Chem. 62, 1135 to 1138 (1990);

g) M. J. Burk et al., Tetrahedron: Asymmetry 2, 569 to 592 (1991).

From the review articles indicated it is also evident that the chiral hydrogenation catalysts can be modified in a wide variety of ways, for example by adsorption or binding (if appropriate via spacers) to inorganic solids (silica gel, activated charcoal, etc.) or immobilized on swellable resins (polymers; see H. Brunner et al., J. Organomet. Chem. 384, 223 (1990)), or can be converted into water-soluble catalysts by means of appropriate highly polar substituents. Immobilized catalysts can be removed from the reaction mixture after the end of the reaction by filtration, thus simplifying the working-up procedure. Sometimes the catalysts isolated by filtration can in addition be used again in subsequent hydrogenation batches without loss of activity or enantioselectivity (recycling). The use of water-soluble catalysts permits the environmentally friendly and inexpensive use of water as solvent and/or the simple removal of the catalyst after the end of hydrogenation by washing with water if a non-polar solvent is used. The use of such modified hydrogenation catalysts in the asymmetric hydrogenation in the context of the enantioselective synthesis of compounds of the formula I is likewise a subject of the present invention.

Ruthenium catalysts are more economic than rhodium catalysts since, firstly, their price on a molar basis is only about a fifth and, secondly, the necessary substrate/catalyst ratio is often more favorable. Possibilities for the recovery of the rhodium after the hydrogenation solutions have been worked up or for the recycling of the total catalyst have been described (W. S. Karoles, Z. Chem. Education 63, 222 (1986) W. Vocke et al., Chem. Techn. 39, 123 (1987); O. Cervinka et al., Czech CS 221, 487, CA 105; 9842 v).

Although, as indicated in the review articles a) to g), a large number of structural types of olefin have been subjected to asymmetric hydrogenation, the asymmetric hydrogenations carried out in the context of the present invention, of the sulfide carboxylic acid VI and/or its ester VII and of the sulfone carboxylic acid XI and/or its ester IX, have no counterpart to date. The only asymmetric hydrogenation of a substrate containing a sulfur atom that is known from the literature is the chiral rhodium(I) diphisphine complex-catalyzed hydrogenation

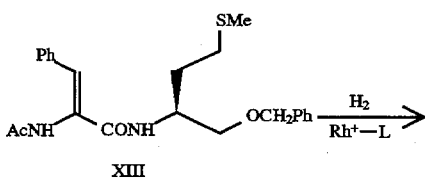

XIII

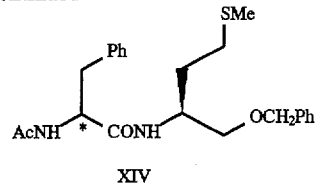

XIV (I. Ojima et al., Tetrahedron 40, 1255 to 1268, on page 1256 (1984)).

This prior art differs fundamentally in a number of ways from the substrates VI, VII, IX and XI of the present invention.

1) As an N-acetyl-dehydro amino acid derivative, compound XIII is the "classical" best-tried olefin structural type for asymmetric hydrogenations based on chiral rhodium catalysts:

a) K. E. Koenig in "Asymmetric Synthesis", Vol. 5, Ed. Morrison, J. D. Academic Press, Orlando 1985, page 71, ff.

b) J. W. ApSimon et al., Tetrahedron 42, 5157 (1986), page 5173 to 5186;

c) H. Brunner, Top. Stereochem. 18, 129 (1988);

d) I. Ojima et al., Tetrahedron 45, 6901 (1989), page 6902 to 6916; the substrates of the present application belong, given the lack of a carbonyl group in the homoallyl position, to an olefin structural type on which it has not been possible hitherto to achieve useful optical inductions with rhodium catalysts. Although α, β-unsaturated carboxylic acids without other functional groups capable of complexation have been hydrogenated using chiral ruthenium catalysts, in some cases with high optical induction, it was unknown in this case whether such catalysts would tolerate sulfur-containing substrates;

e) R. Noyori, H. Takaya, Acc. Chem. Res. 23, 345 (1990);

f) H. Takaya et al., Pure & Appl. Chem. 62, 1135 to 1138 (1990).

2) In compound XIII the sulfur atom is in a position which does not permit the formation of a stable rhodium(I) chelate (in cooperation with one of the two carbonyl groups or the C=C double bond). XIII must therefore behave with regard to the catalyst essentially as if the sulfur functionality was not present. The sulfone group of the present substrates IX and XI or the sulfide group of the present substrates VI and VII, which is in principle capable of complexation, is located, however, in exactly the position in which the classical substrates have the essential carbonyl group. Therefore, whereas the formation of metal chelates is possible in principle, their effect on the course of hydrogenation and on optical induction is not foreseeable.

3) Substrate XIII is already homochiral. The stereoselectivity of the hydrogenation is therefore composed of an enantioselectivity determined by the chiral catalyst and a simple diastereoselectivity determined by the substrate. All of the present substrates VI, VII, IX and XI are prochiral; the optical induction resulting in the hydrogenation is only one property of the catalyst.

The lack up to now in the literature of any asymmetrical hydrogenation of alkenes with sulfur functionality lies apparently in the fact that many organic and inorganic sulfur compounds, especially sulfides, are known to be highly active catalyst poisons for (supported) noble metal catalysts. Correspondingly, even when using crude products of the substrates VI, VII, IX and XI (which are already substantially pure by $^1$H-NMR) under conventional conditions of temperature and hydrogen pressure with chiral diphosphine-rhodium or diphosphine-ruthenium complexes, either no hydrogenation is achieved, or the hydrogenation proceeds very slowly and incompletely, and leads to products of very low optical purity. If the hydrogen pressure and (or) the temperature are increased by a large amount, it is then often possible to bring about a hydrogenation, but this is accompanied, without exception, by very low enantioselectivity (see examples). If, on the other hand, substrates are employed which have been vigorously freed from catalyst poisons, for example by multiple recrystallization, then even under mild conditions rapid, quantitative hydrogenations are achieved, some of which show good optical inductions (see examples).

The inhibition of hydrogenation catalysts by catalyst poisons in crude hydrogenation substrates can be utilized positively in the context of the present invention. When prepared by the Wittig reaction, compounds of the formula VI are generally obtained as E/Z mixtures. A limited influence on the E/Z ratio can be had by choosing the specific conditions of the Wittig reaction, which influence, together with the choice of appropriate solvents for recrystallizations (e.g. in the case of VII), also permits the preparation of diastereomerically pure E-alkenes (see examples).

Under the conditions of the Wittig reaction, which are particularly easy to carry out in a pilot plant, VI is obtained, however, with E/Z ratios within the range from 1:1 to 2:1. In the absence of purifications by recrystallization these also give rise to the other hydrogenation substrates VII, IX and XI with corresponding E/Z ratios.

In asymmetric hydrogenation there is one-sided selectivity, i.e. the chiral catalyst makes the distinction between the top and bottom side of the prochiral double bond and transfers the hydrogen very preferentially to one of these two sides. Thus a E-alkene undergoes transition to a hydrogenation product which is the mirror image of the hydrogenation product of the corresponding Z-alkene. If a catalyst has the maximum of 100% enantioselectivity, which can only be achieved in theory, then it gives a hydrogenation product of 100% ee on a diastereomerically pure substrate alkene (only E or only Z configuration). If the same substrate alkene is present, on the other hand, as an E/Z mixture in a ratio of 1:1, then the same catalyst, if hydrogenation proceeds to completion, gives a racemic hydrogenation product (0% ee). It is evident that, in order to obtain optical purities which are as high as possible, hydrogenation substrates are required whose diastereomeric purity is as high as possible. We have surprisingly found that crude hydrogenation substrates of the formulae VI, VII, IX and XI, which initially have an E/Z ratio of from 1:1 to 2:1, undergo substantially Z→E isomerizations without simultaneous hydrogenation, under the conditions of experimental asymmetric hydrogenations, in the temperature range from 20° to 300° C., preferably from 40° to 150° C. and particularly preferably from 60° to 120° C. Thus a 70:30 E/Z mixture of the sulfone acid XIa is converted, using a neutral rhodium(I)-BPPM catalyst at 120° C. in methanol under 150 atm of hydrogen over the course of 20 hours, into a 97.1:2.9 E/Z mixture of the sulfone carboxylic acid XIa in a yield of 99%. The sulfide carboxylic acid VIIa is converted analogously at 60° C. into 97.5% E isomer of VIIa (see examples).

The E isomers obtained in this way are free from diastereomers (>99.5% E isomer) after recrystallization.

The oxidation of the compounds of the formula VI to give the compounds of the formula IX is possible both directly and also after prior isolation of the sulfoxides. Suitable oxidizing agents are, for example:

Metachloroperbenzoic acid (mCPBA), for example in $CH_2Cl_2$ at from 0° to 25° C.;

Potassium permanganate ($KMnO_4$), for example in $H_2O/K_2CO_3$ at room temperature;

Oxone ($2KHSO_5.KHSO_4.K_2SO_4$) in water at room temperature; Magnesium monoperoxyphthalate (MMPP) in water at room temperature;

$H_2O_2$, 30% strength, at room temperature in $CH_2Cl_2$, in the presence of acetic acid and polyphosphoric acid; $H_2O_2$ is particularly preferred.

The oxidation of the compounds of the formulae VII, VIII and X to give the compounds of the formulae XI, XII and I is possible both directly and also after prior isolation of the sulfoxides. Examples of suitable oxidation means are the reagents and conditions employed for the oxidation of the compounds of the formula VI to give compounds of the formula IX.

The alkaline hydrolysis of the compounds of the formulae VIII, IX and XII to give compounds of the formulae X, XI and I is carried out under conditions analogous to those described for the hydrolysis of compounds of the formula VI to give the compounds of the formula VII.

The chiral compounds of the formulae X, XII and I are prepared by way of an enantioselective hydrogenation of the compounds of the formulae VII, IX and XI under conditions analogous to those described for the enantioselective hydrogenation of the compounds of the formula VI to give the compounds of the formula VIII.

Where the individual reaction products are not already obtained in sufficiently pure form for them to be employed for the following reaction step, purification by crystallization, column chromatography, thin-layer chromatography or high pressure liquid chromatography is advisable.

The compounds of the formulae IV, VI and VII to XII are novel and represent valuable intermediate products for the preparation of compounds of the formula I. The invention therefore also relates to these compounds and to the processes for their preparation as described above.

Note: NMR spectra were measured, unless otherwise indicated, in $CDCl_3$ using TMS as internal standard. The following abbreviations apply to the classification of NMR signals:

s=singlet, d=doublet, p=pentet, t=triplet, q=quartet.

Melting points are uncorrected.

The intention of the following implementation examples and the content of the patent claims is to illustrate the present invention in more detail.

EXAMPLE 1a

Ethyl 3-tert-butylthio-2-oxo-propionate IVa ($R^1$=t-Bu, $R^3$=Et)

10.6 g (25 mmol) of methyltrioctylammonium chloride (Hoechst AG) and 45 g (0.5 mol) of tert-butyl mercaptan are added with stirring at room temperature to a solution of 42 g (0.5 mol) of sodium hydrogen carbonate in 250 ml of water. A solution of 97.5 g (0.5 mol) of ethyl bromopyruvate (Fluka) in 400 ml of methylene chloride is added dropwise with stirring over the course of ½ hour at max. 30° C. with cooling. Stirring is subsequently continued at 20° C. for 2½ hours. The methylene chloride phase is separated off, dried over $MgSO_4$, filtered and concentrated in vacuo.

Yield: 98 g (96% of theory), pale yellow oil $R_f$=0.67 (cyclohexane/ethyl acetate=7:3)

MS: $C_8H_{14}SO_3$ m/e=204

NMR: (CDCl$_3$): δ values (enol form, E/Z) 1.33 (s, t-C$_4$H$_9$), 1.36 (t, OEt), 1.45 (s, t-C$_4$H$_9$) 3.68 (s, SCH$_2$), 4.30 (q, OEt), 4.38 (q, OEt) 5.83 (d, —CH=), 6.53 (d, —CH=), 1.48 (s, OH)

EXAMPLE 2a

1-Naphthylmethyltriphenylphosphonium chloride ($R^2$=1-naphthyl)

340 g (1.93 mol) of 1-chloromethylnaphthalene (Aldrich) are dissolved together with 505.7 g (1.93 mol) of triphenylphosphine in 2 l of acetonitrile. The mixture is subsequently boiled at reflux with stirring for 5 hours. The phosphonium chloride begins to precipitate out after about 2 hours. The mixture is left to cool at room temperature and the crystals are filtered off with suction.

Yield: 798 g (93.9% of theory), white crystals, m.p.: 308° to 310° C.

Analysis: C=79.8, H=5.4, Cl=8.3 found. C=79.0, H=5.5, Cl=8.1 calc.

EXAMPLE 3a 1-tert-Butylthiomethyl-1-ethoxycarbonyl-2-(1-naphthyl) ethylene ($R^1$=t-Bu, $R^2$=1-naphthyl, $R^3$=Et) VIa A suspension of 12.9 g (0.27 mol) of sodium hydride (55% suspension in oil (Fluka)) in 500 ml of absolute tetrahydrofuran is placed under argon in a four-necked flask. 129.1 g (0.29 mol) of 1-naphthylmethyltriphenylphosphonium bromide (Example 2a) is added in portions with stirring over the course of 1 hour while excluding moisture. When the addition is complete, stirring is continued at room temperature for 1 hour. During this period the reaction mixture becomes dark red as the ylide Va ($R^2$=1-naphthyl) is formed. 45.0 g (0.22 mol) of ethyl 3-tert-butylthio-2-oxopropionate IVa (Example 1a) in 100 ml absolute tetrahydrofuran are then added drop-wise to the ylide solution. After stirring for 4 hours at room temperature the reaction mixture is added with stirring to a mixture of 500 ml of saturated sodium chloride solution in water and 500 ml of ethyl acetate. The organic phase is separated off and the aqueous phase is filtered to remove precipitated triphenylphosphine oxide and extracted with 1×300 ml of ethyl acetate. The organic extracts are combined, a little activated charcoal and MgSO$_4$ are added, and the mixture is filtered and concentrated in vacuo. 150 g (>100% of theory) of brown-red oil are obtained. 500 ml of diethyl ether are added to the crude product (150 g), and the mixture is stored overnight at 10° C. in a freezer cabinet. The crystalline triphenylphosphine oxide which is precipitated out is then filtered off and the residue is filtered over a 4 cm thick layer of silica gel. The filtrate is concentrated in vacuo.

Yield: 52 g (71% of theory), pale yellow oil

R$_f$=0.80 (cyclohexane/ethyl acetate=7:3)

MS: C$_{19}$H$_{22}$SO$_2$ m/e=328 δ a value 0.74 (t, OEt); 1.42 (t, OEt); 1.28 and 1.45 (s, tBu); 3.58 and 3.73 (s, SCH$_2$); 3.90 and 4.48 (q, OEt); 7.25 to 8.0 (m, aromatic protons, —CH=) 8.25 (s, —CH=) (E/Z mixture in the ratio of 1:1)

EXAMPLE 4a1

1-tert-Butylthiomethyl-1-carboxy-2-(1-naphthyl)-ethylene ($R^1$=t-Bu, $R^2$=1-naphthyl, $R_3$=H) VIIa 20 g (0.06 mol) of 1-tert-butylthiomethyl-1-ethyloxycarbonyl-2-(1-naphthyl) ethylene VIa (Example 3a) are dissolved in 200 ml of ethanol. 120 ml of 1N NaOH are then added and the mixture is heated under reflux for 1 hour. It is then allowed to cool, 200 ml of ethyl acetate and 200 ml of water are added, and the pH is adjusted to 3 using half-concentrated hydrochloric acid with stirring. The organic phase is separated off and the aqueous phase is extracted with 2×150 ml of ethyl acetate. The combined organic extracts are dried over MgSO$_4$, filtered and concentrated in vacuo.

Yield: 17.0 g (92.8% of theory)

R$_f$=0.13 (cyclohexane/ethyl acetate=7:3)

MS: C$_{17}$H$_{18}$SO$_2$ m/e: 300

NMR: (CDCl$_3$) δ values: 1.29 and 1.46 (s, t-Bu); 3.58 and 3.75 (s, SCH$_2$); 7.8 to 7.95 (m, aromatic protons); 8.25 and 8.42 (s, —CH=) (E/Z mixture in a ratio of 1:1)

EXAMPLE 4a2

Preparation of a pure diastereomer of VIIa by recrystallization of the E/Z mixture 800 ml of cyclohexane are added to 14.3 g of the E/Z mixture from Example 4a1. The mixture is heated for 10 min under a reflux condenser using an oil bath preheated to 100° C. An almost clear solution is formed which is filtered while hot. This filtration removes <100 mg of deep yellow solid. Left standing for two days, at 0° C., the filtrate crystallizes to form a pale yellow solid which is filtered off with suction and dried under a high vacuum.

This recrystallization is repeated twice. 4.8 g (67% of theory) of a pale yellow solid are obtained which has a melting point of 167° to 168° C. and which according to HPLC contains <0.5% of the diastereomer.

NMR (CDCl$_3$) δ values: 1.30 (s, t-Bu); 3.60 (s, SCH$_2$); 7.46 to 7.63 (m, 3H, aromatic-H); 7.84 to 8.02 (m, 4H, aromatic-H), 8.44 (s, 1H, =CH);

MS and TL as described above.

EXAMPLE 4a3

Preparation of a pure diastereomer of VIIa by Z→E isomerization

A solution of 3.0 g (10.0 mmol) of the E/Z mixture VIIa in 100 ml of methanol is degassed by bubbling through argon. 10 mg (0.02 mmol) of chloro(1,5-cyclooctadiene)-rhodium(I) dimer (Fluka), 27.7 mg (0.05 mmol) of (2S, 4S)-(−)-N-tert-butoxycarbonyl-4-diphenylphosphino-2-diphenylphosphinomethylpyrrolidine ((−)-BPPM, Merck-Schuchardt) and 1.11 g (11.0 mmol) of triethylamine are added under argon. The reaction mixture is shaken at 60° C. for 16 hours under 50 atm of hydrogen. HPLC analysis of the reaction mixture under the conditions of Example 7a reveals 97.5% (E)-VIIa, 2% (Z)-VIIa and 0.5% hydrogenation product X. The mixture is worked up as in Example 7a to give 2.9 g (97% of theory) of (E)-VIIa. Recrystallization of this product as in Example 4a2 gives 2.4 g (80% of theory based on the E/Z-VIIa employed) of (E)-VIIa which according to HPLC contains <0.5% of the diastereomer. This product is identical with that of Example 4a2 with regard to its melting point and $^1$H-NMR data.

EXAMPLE 5a

Ethyl 3-tert-butylthio-2(S)-(1-naphthylmethyl)propionate ($R^1$=t-Bu, $R^2$=1-naphthyl, $R^3$=Et) VIII this example must be submitted at a later point in time

EXAMPLE 6a 1-tert-Butylsulfonylmethyl-1-ethoxycarbonyl-2-(1-naphthyl)-ethylene ($R^1$=t-Bu, $R^2$=1-naphthyl, $R^3$=Et) IXa 16 g (48 mmol) of 1-tert-butylthiomethyl-1-ethoxycarbonyl-2-(1-naphthyl)-ethylene VIa (Example 3a) are dissolved in 160 ml of ethyl acetate and 9.6 ml (160 mmol) of glacial acetic acid. 16 ml (160 mmol) of 30% strength hydrogen peroxide are added dropwise with stirring at room temperature. The mixture is then stirred at room temperature for 3 hours, and 200 ml of water and 200 ml of ethyl acetate are added. The organic phase is separated off, washed free of acid with sodium hydrogen carbonate solution, dried over $MgSO_4$ and concentrated in vacuo.

Yield: 14 g (83% of theory) of white crystals, m.p.=94° to 98° C.

$R_f$=0.28 and 0.38 (cyclohexane/ethyl acetate=7:3)

MS: $C_{20}H_{24}SO_4$ m/e 360

NMR: ($CDCl_3$) δ values: 1.28 and 1.43 (t, OEt), 1.36 and 1.54 (s, t-Bu); 3.90 and 4.41 (q, OEt); 4.21 and 4.28 (s, $CH_2CO_2$); 7.30 to 7.05 (m, aromatic protons); 7.92 and 8.58 (s, —CH=) (E/Z mixture in a ratio of 1:1)

EXAMPLE 7a 3-tert-Butylthio-2-(S)-(1-naphthylmethyl) propionic acid ($R^1$=t-Bu, $R^2$=1-naphthyl, $R^3$=H) X 3.0 g (10 mmol) of 1-tert-butylthiomethyl-1-carboxy-2-(E)-(1-naphthyl) ethylene VIIa (Example 4a, <0.5% of the Z isomer) are dissolved in 500 ml of methanol in a glass insert for a steel autoclave and are degassed by bubbling through argon. 621 mg (0.1 mmol) of (S)-(−)-2,2'-bis-(diphenylphosphino)-1,1'-binaphthalene ((S)-(−)-BINAP, Strem Chemicals) and 26 mg (0.05 mmol) of benzene ruthenium(II) chloride dimer (Aldrich) are dissolved in 50 ml of dimethylformamide under argon in a different vessel, then heated at 100° C. for 10 minutes and cooled again to 25° C., in each case under argon. An argon-degassed solution of 171 mg (30.8 mmol) of sodium acetate in 20 ml of methanol is added, the mixture is stirred at 25° C. for 5 minutes and the resulting catalyst solution is poured in under argon to the substrate solution in the glass insert. The glass insert is placed in an argon-filled autoclave. The argon atmosphere is displaced by hydrogen. The reaction solution is shaken at 120° C. for 20 hours under a hydrogen pressure of 150 atm. The autoclave is flushed with nitrogen, the glass insert is withdrawn, the solvent is removed in vacuo and the residue is taken up in 300 ml of methyl tert-butyl ether. This mixture is shaken with 100 ml of 0.5N hydrochloric acid for 2 minutes. The organic phase is separated off and the aqueous phase is extracted with 100 ml of MTB ether. The combined organic phases are washed with 50 ml of 0.5N hydrochloric acid and 50 ml of water and dried over magnesium sulfate. The solvent is removed in vacuo and the oil which remains is dried under a high vacuum. The product (3.01 g, 9.95 mmol, 99.5% of theory) according to HPLC has a purity of 98% {250×4.00 mm ®Nucleosil 100 C18 7 μm, detector 300 nm, 1.5 ml/min [51% water/49% acetonitrile +0.05% $NH_4H_2PO_4$ adjusted to pH=3.5 with 85% strength phosphoric acid], ($t_{ref}$: (Z)-VII 15.2 min), X 16.8 min, (E)-VIIa 18.50 min}. $[\alpha]_D^{25}$=2.30° (c=1.06, derivatization with MEPA/optically pure (R)-(+)-1-phenylethylamine followed by HPLC separation on RP18-®LiChrospher 100 with acetonitrile/water 1:1 gives the peaks of the two diastereomeric amides in a ratio of 85:15. (S)-X therefore has 70% ee.

EXAMPLE 8a

The unsaturated (E)-sulfide carboxylic acid VIIa is converted into the saturated (S)-sulfide carboxylic acid (S)-X by a number of different asymmetric hydrogenations. Hydrogenating conditions as well as the respective yield and optical purity of the hydrogenation product can be taken from Table 1.

TABLE 8a

Table 1: Asymmetric hydrogenations of the sulfide carboxylic acid of the formulae VIIa to Xa

| Formula | Catalyst isolated/generated in situ | Substrate/Catalyst ratio (mmol/mmol) | $H_2$ Pressure (bar) | Temp. (°C.) | Hydrogenation (time) | Conversion (%)[a] | Optical purity of Xa (% ee) |
|---|---|---|---|---|---|---|---|
| (BINAP-Ru structure) | isolated | 100 | 150 | 150 | 1/6 | 30 | 43 |
|  | isolated | 100 | 150 | 150 | 1 | 100 | 65 |
|  | isolated | 100 | 150 | 120 | 5 | 100 | 70 |
|  | in situ | 100 | 150 | 120 | 20 | 100 | 72 |
|  | isolated | 100 | 150 | 80 | 6 | 100 | 72 |
|  | isolated | 100 | 150 | 50 | 48 | 100 | 39 |
|  | isolated | 100 | 150 | 25 | 96 | 100 | 54 |
|  | isolated | 100[b] | 150 | 50 | 48 | 100 | 0 |
| (Pyrrolidine-PPh2 structure) [Rh(COD)2]+BF4− | in situ | 200 | 1 | 20 | 24 | 17 | 0 |
|  |  | 200 | 100 | 20 | 20 | 98 | 52 |
|  |  | 100 | 30 | 50 | 20 | 99 | 43 |
|  |  | 100 | 150 | 50 | 20 | 100 | 48 |
|  |  | 50 | 150 | 120 | 20 |  | 46 |

TABLE 8a-continued

Table 1: Asymmetric hydrogenations of the sulfide carboxylic acid of the formulae VIIa to Xa

| Formula | Catalyst | isolated/generated in situ | Substrate/ Catalyst ratio (mmol/mmol) | H$_2$ Pressure (bar) | Temp. (°C.) | Hydrogenation (time) | Conversion (%)[a] | Optical purity of Xa (% ee) |
|---|---|---|---|---|---|---|---|---|
| 4 | [(COD)Rh(Ph$_2$P-CH$_2$-CH(N-C(=O)-N-Ph-H)-CH$_2$-PPh$_2$)] BF$_4^-$ | isolated | 50 | 150 | 120 | 20 | ~100° | 4 | a) % of product Xa based on the sum of % of product Xa and % of starting material VIIa b) in the presence of 1.05 equivalents (based on VIIa) of triethylamine c) the starting material VIIa has completely disappeared. In addition to 80% of Xa, 20% of impurities are formed.

EXAMPLE 9a 1-tert-Butylsulfonylmethyl-1-carboxy-2-(1-naphthyl)-ethylene (R$^1$=t-Bu, R$^2$=1-naphthyl, R$^3$=H) XIa 17 g (56 mmol) of 1-tert-butylthiomethyl-1-carboxy-2-(1-naphthyl)ethylene VIIa (Example 4a) are dissolved in 170 ml of ethyl acetate and 10 ml of glacial acetic acid. 17 ml (170 mmol) of 30% strength hydrogen peroxide are added dropwise with stirring at room temperature. The mixture is then stirred at room temperature for 5 hours. 200 ml of ethyl acetate are added, and the organic phase is extracted with 5×100 ml of saturated sodium chloride solution. The organic phase is separated off, dried over MgSO$_4$ and concentrated in vacuo, an additional 100 ml of ethyl acetate are added if required, and the mixture is again concentrated in vacuo on a rotary evaporator in order to remove residual glacial acetic acid. 90 ml of methyl tert-butyl ether are added to the residue, and the mixture is crystallized overnight in a freezer cabinet.

Yield: 14.8 g (80% of theory) of pale yellow crystals, m.p. 80° C.

R$_f$=0.30 and 0.52 (cyclohexane/ethyl acetate/AcOH= 20:80:1)

MS: C$_{18}$H$_{20}$SO$_4$ m/e=332

NMR: (CDCl$_3$) δ value: 1.33 and 1.55 (s, t-Bu); 4.20 and 4.28 (s, CH$_2$SO$_2$); 7.4 to 8.1 (m, aromatic protons), 7.48 and 8.73 (s, —CH=) (E/Z mixture in a ratio of 1:1)

Removal of catalyst poisons by recrystallization:

400 ml of n-heptane were added to 11.9 g of the above crude carboxylic acid (E/Z~2:1) and the mixture was heated at reflux. Methyl tert-butyl ether is poured in portions through the reflux condenser into the boiling suspension. After addition of 200 ml of MTB ether, an almost clear solution is formed. Small quantities (<100 mg) of solid are filtered off hot with suction and discarded. The filtrate is left to cool slowly to room temperature (again a clear solution), about 20 mg of seed crystals are added, and the mixture is cooled at 0° C. for several hours and then at −20° C. for one day. The crystals are filtered off with suction, washed with 2=100 ml of n-heptane and dried for 2 days under a high vacuum. 8.0 g of white crystals are obtained which according to $^1$H-NMR have a E/Z ratio of ~2:1 and contain 0.5 mol of MTB ether m.p. 96° to 105° C. Further drying under a high vacuum at 80° C. for 8 hours gives 7.0 g of gray crystals which no longer contain any MTB ethers; m.p. 100° to 115° C.

EXAMPLE 10a 1-tert-Butylsulfonylmethyl-1-carboxy-2-(1-naphthyl)-ethylene (R$^1$=t-Bu, R$^2$=1-naphthyl, R$^3$=H) XIa 13 g (36 mmol) of 1-tert-butylsulfonylmethyl-1-ethyloxycarbonyl-2-(1-naphthyl)ethylene IXa (Example 6a) are dissolved in 130 ml of ethanol. Then 80 ml of 1N sodium hydroxide solution are added and the mixture is stirred at 50° C. for 1½ hours. The mixture is cooled, 200 ml of ethyl acetate and 200 ml of water are added, half-concentrated hydrochloric acid is added, and the aqueous phase is again extracted with 200 ml of ethyl acetate. The combined organic phases are dried over MgSO$_4$, filtered and concentrated in vacuo. The residue (15 g) is recrystallized from 50 ml of methyl tert-butyl ether and stored overnight in a freezer cabinet.

Yield: 11.6 g (96% of theory) of pale yellow crystals, m.p. 80° C.

R$_f$=0.30 and 0.52 (cyclohexane/ethyl acetate/AcOH= 20:80:1)

MS: C$_{18}$H$_{20}$SO$_4$ m/e=332

NMR: (CDCl$_3$) δ values: analogous to Ex. 8a (E/Z mixture in a ratio of 1:1)

EXAMPLE 11a 3-tert-Butylsulfonyl-2(S)-(1-naphthylmethyl)propionic acid (R$^1$=t-Bu, R$^2$=1-naphthyl, R$^3$=H) I by oxidation of X 681 mg (2.25 mmol) of 3-tert-butylthio-2(S)-(1-naphthylmethyl) propionic acid of 70% ee (Example 7a) are dissolved in 450 μl of glacial acetic acid and 1.35 ml of dichloromethane. 0.75 ml (8.7 mmol) of 35% strength aqueous hydrogen peroxide solution are added with ice cooling, and the mixture is stirred at 0° C. for 1 hour. HPLC indicates almost complete conversion of the starting material with the formation of predominantly sulfoxide and a little sulfone.

10 g of polyphosphoric acid are dissolved in 10 g of 85% strength ortho-phosphoric acid, and 200 μl of this solution are added to the above reaction solution, and the mixture is stirred at room temperature for 3 hours. HPLC indicates complete oxidation of the sulfoxide to the sulfone. 10 ml of dichloromethane and 10 ml of water are added and mixed in by shaking. The organic phase is separated off and the aqueous phase is extracted with 2×10 ml of dichloromethane. The combined organic phases are washed with 3×5 ml of 10% strength sodium bisulfite solution and then with 2×3 ml of water, dried over magnesium sulfate and filtered. The solvent is removed in vacuo and the residue is dried under a high vacuum. 680 mg (90% of theory) of a pale yellow solid foam are obtained, $[\alpha]_D^{25} = +1.19°$ (c=0.98, $CH_3OH$). Derivatization with MEPA/optically pure (R)-(+)-1-phenylethylamine followed by HPLC analysis as in Example 7a gives a 74% ee.

The oxidation is therefore not associated with any reduction in optical purity.

MS: $C_{18}H_{22}SO_4$ m/e=334

NMR ($CDCl_3$) δ values: 1.27 (s, t-Bu) 3.00 to 3.18 (m, 1H, CH—$CO_2H$); 3.35 to 3.80 (m, 4H, 2×$CH_2$); 5.40 to 6.70 (very broad s, 1H, $CO_2H$); 7.33 to 7.65 (m, 4H, aromatic-H); 7.75 to 7.90 (ddd, 2H, aromatic-H); 8.13 (d, 1H, aromatic-H).

550 mg of this product of 74% ee are dissolved entirely in 5 ml of toluene/MTB ether 7:3. The solution is left to stand in a flask at room temperature for 4 days permitting the solvent to evaporate slowly. About half of the solvent evaporates within the period indicated, and the product crystallizes in the form of large platelets. The mother liquor is concentrated to dryness in vacuo.

Crystals: 170 mg, 16% ee from mother liquor: 370 mg, 96% ee.

EXAMPLE 12a 3-tert-Butylsulfonyl-2(S)-(1-naphthylmethyl)-propionic acid ($R^1$=t-Bu, $R^2$=1-naphthyl, $R^3$=H) I by hydrolysis of XII The hydrolysis is completely analogous to that of Example 10a.

Derivatization with MEPA/optically pure (R)-(+)-1-phenylethylamine followed by HPLC analysis as in Example 7a demonstrates that the hydrolysis is not associated with any reduction in optical purity.

The spectra of the product correspond to those of Example 11a.

We claim:

1. A process for the stereoselective preparation of a compound of the formula I

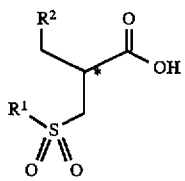

in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or is substituted by 1, 2 or 3 identical or different hydroxyl, methoxy or trialkylsilyloxy groups; and $R^2$ is $C_6$–$C_{12}$-aryl which is unsubstituted or is substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups, and the compound of the formula I may be present in the R or S form, which process comprises I) reacting a mercaptan of the formula II $$R^1\text{—SH} \qquad \text{II}$$

in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; in the presence of a base with a compound of the formula III

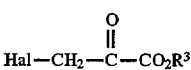

in which Hal is iodine, bromine or chlorine and $R^3$ is a straight-chain or branched alkyl radical having 1 to 6 carbon atoms, to give a compound of the formula IV

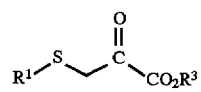

in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^3$ is a straight-chain or branched alkyl radical having 1 to 6 carbon atoms, and II) reacting the compound of the formula IV with an ylide of the formula V $$R^2\text{—CH=P}(C_6H_5)_3 \qquad \text{V}$$

in which $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkyl, which is unsubstituted or substituted by 1, 2 or 3 identical or different methoxy, halogen, cyano, methyl, trifluoromethyl, isopropyl or nitro groups to give an unsaturated compound of the formula VI

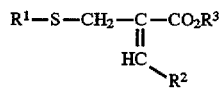

in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and $R^3$ is a straight-chain or branched alkyl radical having 1 to 6 carbon atoms, and III) converting the compound of the formula VI into a compound of the formula I, by A) subjecting the compound of the formula VI to alkaline hydrolysis to give a compound of the formula VII

VII in which $R^1$ is $C_1$–$C_6$-alkyl, $C_3$–$C_6$-cycloalkyl, $(C_6$–$C_{12})$-aryl-$(C_1$–$C_4)$-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and a) by enantioselective hydrogenation, converting the compound of the formula VII into a compound of the formula X

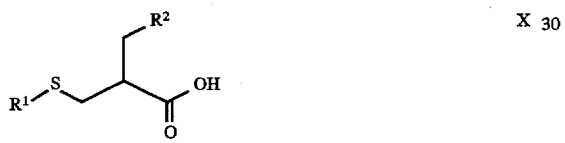
X in which $R^1$ is $C_1$–$C_6$-alkyl, $C_3$–$C_6$-cycloalkyl, $(C_6$–$C_{12})$-aryl-$(C_1$–$C_4)$-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and, by subsequent oxidation, converting the compound of the formula X into a compound of the formula I, or b) by oxidation, reacting the compound of the formula VII to give a compound of the formula XI

XI in which $R^1$ is $C_1$–$C_6$-alkyl, $C_3$–$C_6$-cycloalkyl, $(C_6$–$C_{12})$-aryl-$(C_1$–$C_4)$-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and, by subsequent enantioselective hydrogenation of the compounds of the formula XI, obtaining a compound of the formula I, or B) subjecting the compound of the formula VI to enantioselective hydrogenation with a chiral catalyst to give a compound of the formula VIII

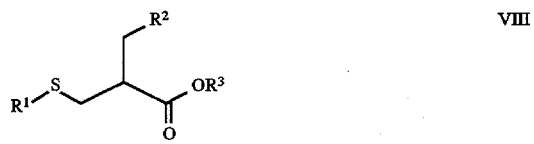
VIII in which $R^1$ is $C_1$–$C_6$-alkyl, $C_3$–$C_6$-cycloalkyl, $(C_6$–$C_{12})$-aryl-$(C_1$–$C_4)$-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and $R^3$ is a straight-chain or branched alkyl radical having 1 to 6 carbon atoms, and a) by alkaline hydrolysis, converting the compound of the formula VIII into a compound of the formula X

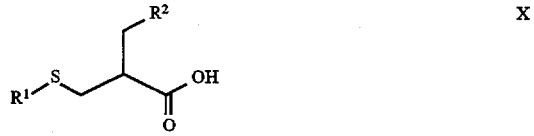
X in which $R^1$ is $C_1$–$C_6$-alkyl, $C_3$–$C_6$-cycloalkyl, $(C_6$–$C_{12})$-aryl-$(C_1$–$C_4)$-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and, by subsequent oxidation of the compound of the formula X, obtaining a compound of the formula I, or b) by oxidation of the compound of the formula VIII, obtaining a compound of the formula XII

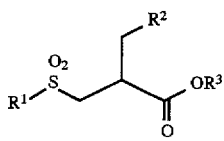

XII in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; is or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and $R^3$ is a straight-chain or branched alkyl radical having 1 to 6 carbon atoms, and subsequently, by alkaline hydrolysis, converting the compound of the formula XII into a compound of the formula I, or c) oxidizing the compound of the formula VI to give a compound of the formula IX

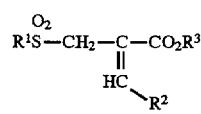

IX in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and $R^3$ is a straight-chain or branched alkyl radical having 1 to 6 carbon atoms, and converting the compound of the formula IX into a compound of the formula I by a) alkaline hydrolysis of the compound of the formula IX to give a compound of the formula XI,

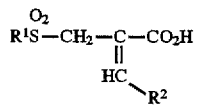

XI in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and subsequent enantioselective hydrogenation of the compound of the formula XI to give a compound of the formula I, or b) enantioselective hydrogenation of the compound of the formula IX to give a compound of the formula XII

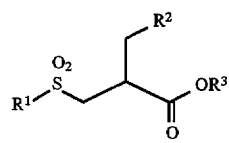

XII in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl, which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups; is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl, which is unsubstituted or substituted by 1, 2 or 3 identical or different methoxy, halogen, cyano, methyl, trifluoromethyl, isopropyl or nitro groups; and $R^3$ is a straight-chain or branched alkyl radical having 1 to 6 carbon atoms, and subsequent alkaline hydrolysis of the compound of the formula XII to give a compound of the formula I.

2. The process as claimed in claim 1, wherein $R^1$ is $C_1$–$C_4$-alkyl, $C_5$–$C_6$-cycloalkyl, ($C_6$–$C_{12}$)-aryl-($C_1$–$C_3$)-alkyl or $C_6$–$C_{12}$-aryl or heteroaryl, which may be substituted by a hydroxyl, methoxy or trialkylsilyloxy group; and $R^2$ is a $C_6$–$C_{12}$-aryl which may be substituted by a methoxy, halogen, methyl, trifluoromethyl or isopropyl group;

is $C_3$–$C_6$-heteroaryl which may be substituted by a methoxy, halogen, methyl, trifluoromethyl, or isopropyl group, or is $C_1$–$C_4$-alkyl, -alkenyl or -alkynyl.

3. The process as claimed in claim 1 and 2, wherein $R^1$ is $C_1$–$C_4$-alkyl, ($C_6$–$C_{12}$)-aryl-($C_1$–$C_3$)-alkyl or $C_6$–$C_{12}$-aryl, and $R^2$ is $C_6$–$C_{12}$-aryl, $C_3$–$C_6$-heteroaryl or $C_1$–$C_4$-alkyl, -alkenyl or -alkynyl.

* * * * *

UNITED STATES PATENT AND TRADEMARK OFFICE
CERTIFICATE OF CORRECTION

PATENT NO.   :   5,684,185
DATED        :   November 04, 1997
INVENTOR(S)  :   Gerhard BECK et al.

It is certified that error appears in the above-indentified patent and that said Letters Patent is hereby corrected as shown below:

Claim 1, column 23, line 18, after "groups;", delete "is".

Claim 1, column 24, line 1, after "groups", insert --;--.

Signed and Sealed this

Fifth Day of May, 1998

Attest:

BRUCE LEHMAN

Attesting Officer          Commissioner of Patents and Trademarks